(12) United States Patent
Laubert

(10) Patent No.: US 9,211,193 B2
(45) Date of Patent: Dec. 15, 2015

(54) PROSTHESIS, SYSTEM AND METHOD

(71) Applicant: AESCULAP IMPLANT SYSTEMS, LLC, Center Valley, PA (US)

(72) Inventor: Nikolay Laubert, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 159 days.

(21) Appl. No.: 14/015,623

(22) Filed: Aug. 30, 2013

(65) Prior Publication Data

US 2015/0066146 A1    Mar. 5, 2015

(51) Int. Cl.
     *A61F 2/44*      (2006.01)
     *A61F 2/30*      (2006.01)

(52) U.S. Cl.
CPC . *A61F 2/442* (2013.01); *A61F 2/44* (2013.01); *A61F 2002/3042* (2013.01); *A61F 2002/3055* (2013.01); *A61F 2002/30507* (2013.01); *A61F 2002/30523* (2013.01); *A61F 2002/30601* (2013.01); *A61F 2002/4475* (2013.01)

(58) Field of Classification Search
CPC ... A61F 2/442; A61F 2/44; A61F 2002/3042; A61F 2002/30507; A61F 2002/30523; A61F 2002/3055; A61F 2002/30601; A61F 2002/4475
USPC .................. 606/246; 623/17.11, 17.15, 17.16
See application file for complete search history.

(56) References Cited

U.S. PATENT DOCUMENTS

| | | | |
|---|---|---|---|
| 5,336,223 A | 8/1994 | Rogers | |
| 5,571,192 A | 11/1996 | Schonhoffer | |
| 5,702,453 A | 12/1997 | Rabbe et al. | |
| 5,702,455 A | 12/1997 | Saggar | |
| 5,776,198 A | 7/1998 | Rabbe et al. | |
| 5,989,290 A | 11/1999 | Biedermann et al. | |
| 6,126,660 A | 10/2000 | Dietz | |
| 6,176,881 B1 | 1/2001 | Schar et al. | |
| 6,193,755 B1 | 2/2001 | Metz-Stavenhagen et al. | |
| 6,193,756 B1 * | 2/2001 | Studer et al. | ............... 623/17.15 |
| 6,200,348 B1 | 3/2001 | Biedermann et al. | |
| 6,344,057 B1 | 2/2002 | Rabbe et al. | |

(Continued)

FOREIGN PATENT DOCUMENTS

| | | |
|---|---|---|
| EP | 1 212 992 A2 | 6/2002 |
| EP | 1 361 840 B1 | 9/2005 |

(Continued)

OTHER PUBLICATIONS

International Search Report for PCT/US2014/053538 dated Dec. 18, 2014.

*Primary Examiner* — Pedro Philogene
*Assistant Examiner* — David C Comstock
(74) *Attorney, Agent, or Firm* — Kenealy Vaidya LLP

(57) ABSTRACT

An implant device, system and method can include a top structure, a bottom structure, and an intermediary structure. The bottom structure can include a helical groove structure, and the intermediary structure can include at least one pin that cooperates with the helical groove structure such that the pin and the helical groove structure guide the intermediary structure in both a rotational direction about the central axis and an axial linear direction along the central axis. The bottom structure can also include a linear groove structure configured to guide the top structure in a linear motion with respect to the bottom structure when the intermediary structure is rotated with respect to the bottom structure.

20 Claims, 11 Drawing Sheets

(56) References Cited

U.S. PATENT DOCUMENTS

| | | | |
|---|---|---|---|
| 6,524,341 B2 * | 2/2003 | Lang et al. | 623/17.15 |
| 6,752,832 B2 | 6/2004 | Neumann | |
| 6,902,579 B2 | 6/2005 | Harms et al. | |
| 7,029,498 B2 | 4/2006 | Boehm et al. | |
| 7,056,343 B2 | 6/2006 | Schafer et al. | |
| 7,156,874 B2 * | 1/2007 | Paponneau et al. | 623/17.11 |
| 7,238,205 B2 | 7/2007 | Karahalios | |
| 7,285,134 B2 | 10/2007 | Berry et al. | |
| 7,458,988 B2 | 12/2008 | Trieu et al. | |
| 7,544,208 B1 | 6/2009 | Mueller et al. | |
| 7,547,325 B2 | 6/2009 | Biedermann et al. | |
| 7,674,296 B2 * | 3/2010 | Rhoda et al. | 623/17.15 |
| 7,909,870 B2 * | 3/2011 | Kraus | 623/17.11 |
| 7,981,157 B2 | 7/2011 | Castleman et al. | |
| 8,062,366 B2 | 11/2011 | Melkent | |
| 8,241,363 B2 * | 8/2012 | Sommerich et al. | 623/17.16 |
| 8,252,054 B2 | 8/2012 | Greenhalgh et al. | |
| 8,257,442 B2 | 9/2012 | Edie et al. | |
| 8,308,802 B2 | 11/2012 | Rhoda et al. | |
| 8,337,558 B2 | 12/2012 | Lindner | |
| 8,337,559 B2 | 12/2012 | Hansell et al. | |
| 8,449,574 B2 | 5/2013 | Biedermann et al. | |
| 2005/0090898 A1 | 4/2005 | Berry et al. | |
| 2005/0107878 A1 | 5/2005 | Conchy | |
| 2005/0113921 A1 | 5/2005 | An et al. | |
| 2005/0154459 A1 | 7/2005 | Wolek et al. | |
| 2005/0187625 A1 | 8/2005 | Wolek et al. | |
| 2005/0209697 A1 | 9/2005 | Paponneau et al. | |
| 2006/0058877 A1 | 3/2006 | Gutlin et al. | |
| 2007/0123987 A1 | 5/2007 | Bernstein | |
| 2007/0255407 A1 | 11/2007 | Castleman et al. | |
| 2008/0039948 A1 | 2/2008 | Biedermann et al. | |
| 2008/0161926 A1 | 7/2008 | Melkent et al. | |
| 2008/0167720 A1 | 7/2008 | Melkent | |
| 2008/0243254 A1 | 10/2008 | Butler | |
| 2008/0281424 A1 | 11/2008 | Parry et al. | |
| 2008/0288071 A1 | 11/2008 | Biyani et al. | |
| 2009/0105835 A1 | 4/2009 | Hovda et al. | |
| 2009/0112324 A1 | 4/2009 | Refai et al. | |
| 2009/0138089 A1 * | 5/2009 | Doubler et al. | 623/17.16 |
| 2009/0164017 A1 | 6/2009 | Sommerich et al. | |
| 2009/0164018 A1 | 6/2009 | Sommerich et al. | |
| 2009/0164019 A1 | 6/2009 | Hsu et al. | |
| 2009/0270987 A1 | 10/2009 | Heinz et al. | |
| 2010/0082106 A1 | 4/2010 | Muhanna | |
| 2011/0106258 A1 | 5/2011 | Blackwell et al. | |
| 2011/0178598 A1 | 7/2011 | Rhoda et al. | |
| 2011/0184524 A1 | 7/2011 | Wiedenbeck et al. | |
| 2011/0257745 A1 | 10/2011 | Miller et al. | |
| 2012/0016476 A1 | 1/2012 | Wilfong et al. | |
| 2012/0029635 A1 | 2/2012 | Schoenhoeffer et al. | |
| 2012/0130493 A1 * | 5/2012 | McLaughlin et al. | 623/17.16 |
| 2012/0303130 A1 | 11/2012 | Winslow et al. | |
| 2012/0316652 A1 | 12/2012 | Renganath et al. | |
| 2012/0330426 A1 | 12/2012 | McLaughlin et al. | |
| 2013/0006358 A1 | 1/2013 | Olevsky et al. | |
| 2013/0006359 A1 | 1/2013 | Fedorov et al. | |

FOREIGN PATENT DOCUMENTS

| | | |
|---|---|---|
| EP | 1 135 076 B1 | 11/2005 |
| EP | 1 501 453 B1 | 12/2005 |
| EP | 1 049 431 B1 | 5/2006 |
| EP | 1 721 583 A2 | 11/2006 |
| EP | 1 872 748 A1 | 1/2008 |
| EP | 1 620 044 B1 | 3/2008 |
| EP | 1 608 298 B1 | 12/2008 |
| EP | 1 341 491 B1 | 4/2009 |
| EP | 1 589 906 B1 | 4/2009 |
| FR | 2 929 106 A1 | 10/2009 |
| FR | 2 929 829 A1 | 10/2009 |
| WO | 2004/103226 A2 | 12/2004 |
| WO | 2005/041824 A2 | 5/2005 |
| WO | 2005/055887 A2 | 6/2005 |
| WO | 2007/148012 A2 | 12/2007 |
| WO | 2008/033457 A2 | 3/2008 |
| WO | 2008/076679 A1 | 6/2008 |
| WO | 2008/148210 A1 | 12/2008 |
| WO | 2008/152499 A2 | 12/2008 |
| WO | 2009/023016 A1 | 2/2009 |
| WO | 2009/079502 A1 | 6/2009 |
| WO | 2009/091629 A2 | 7/2009 |
| WO | 2009/120618 A2 | 10/2009 |
| WO | 2011/060071 A1 | 5/2011 |
| WO | 2011/134457 A1 | 11/2011 |
| WO | 2013/119803 A1 | 8/2013 |

* cited by examiner

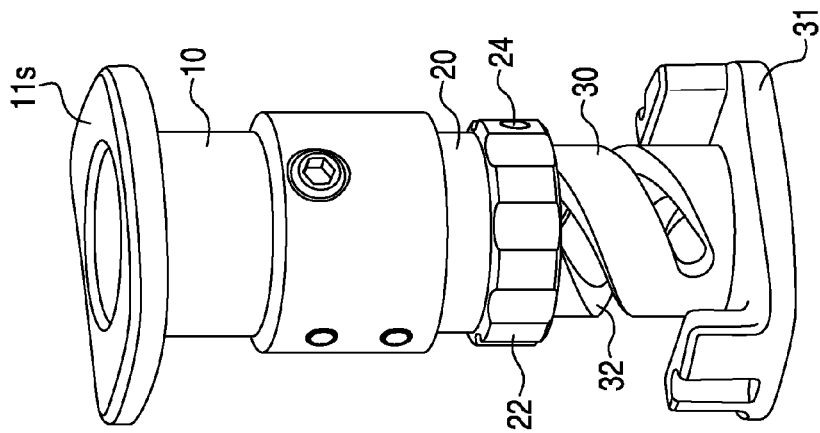
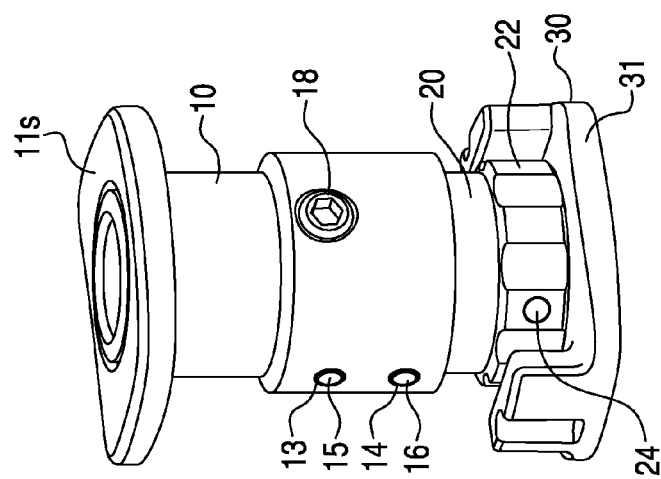

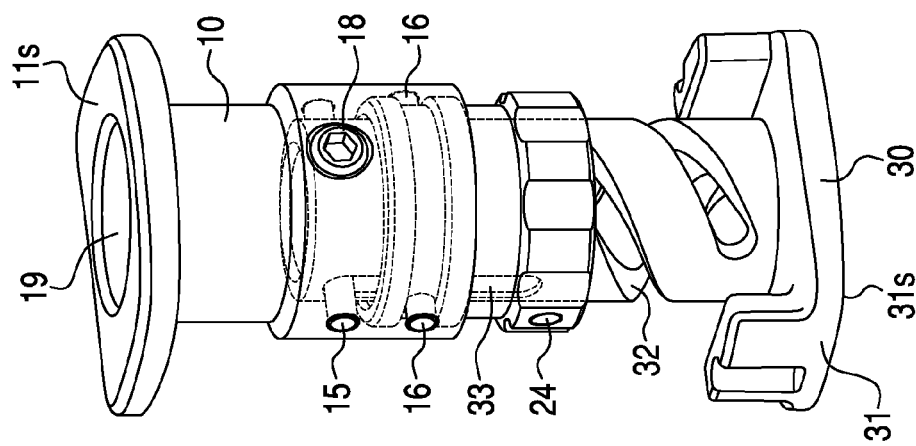
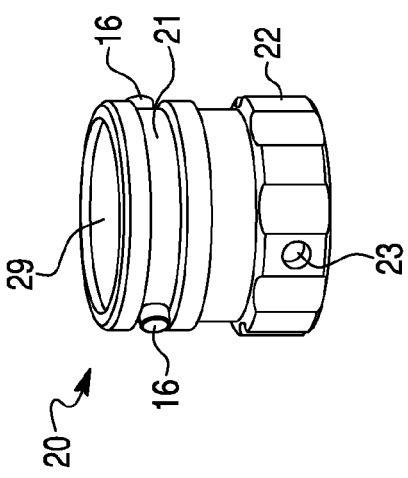
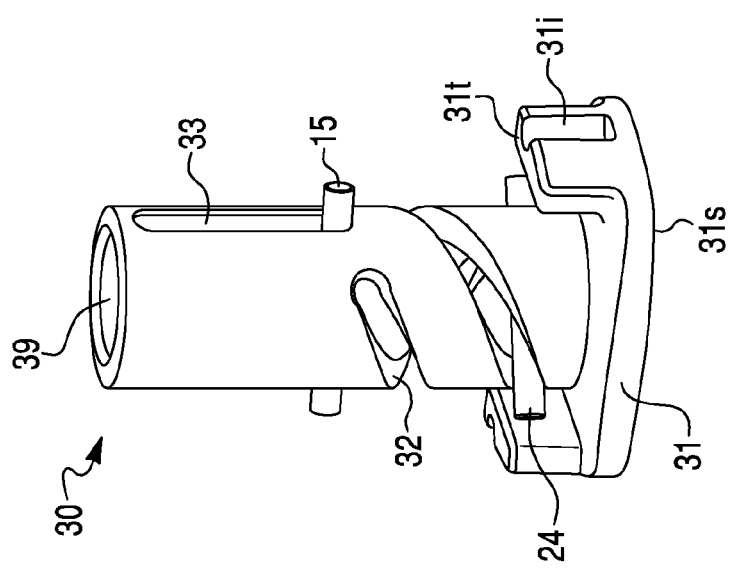

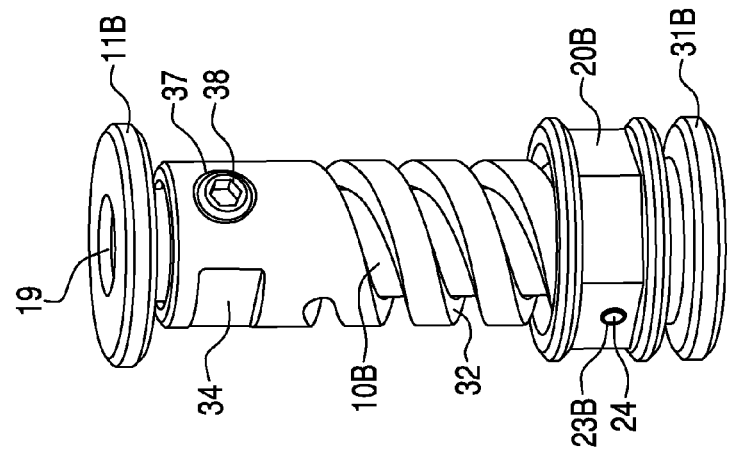
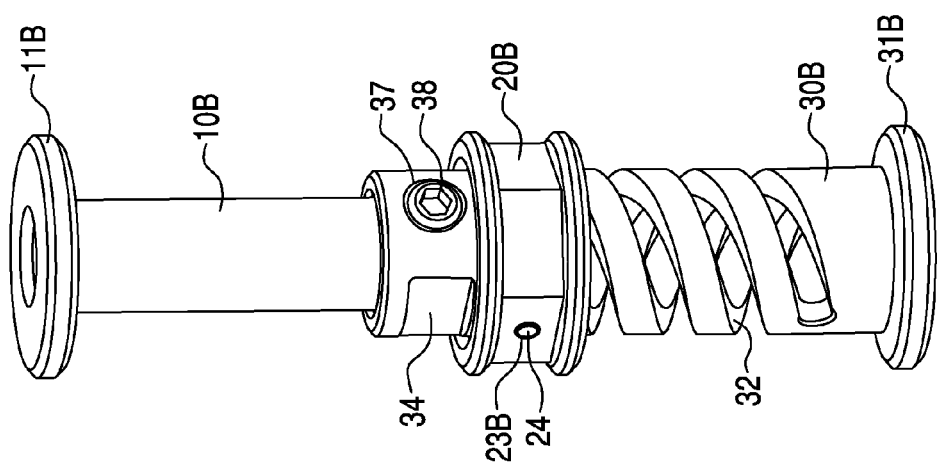
Fig. 7B
Fig. 7A

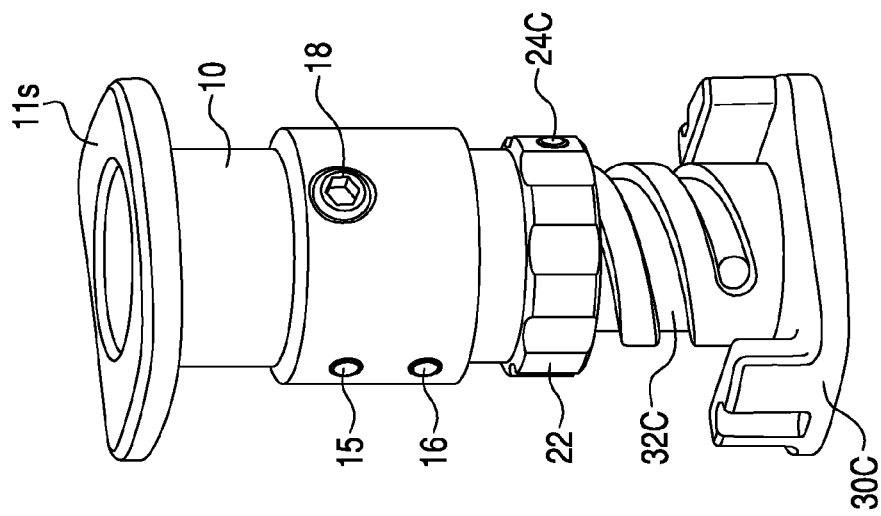
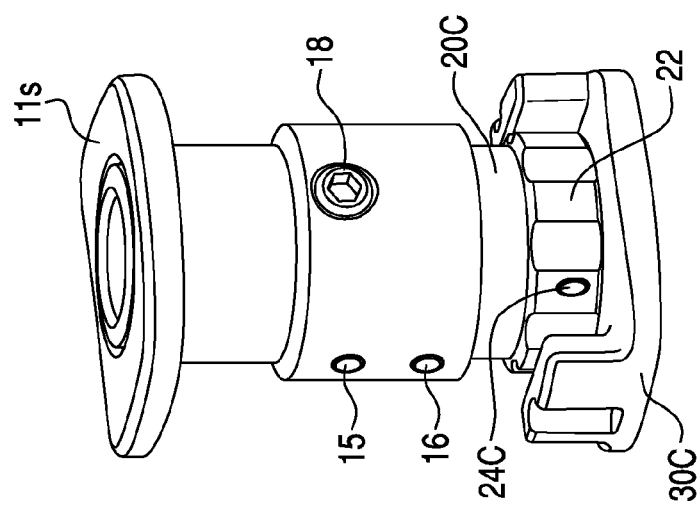

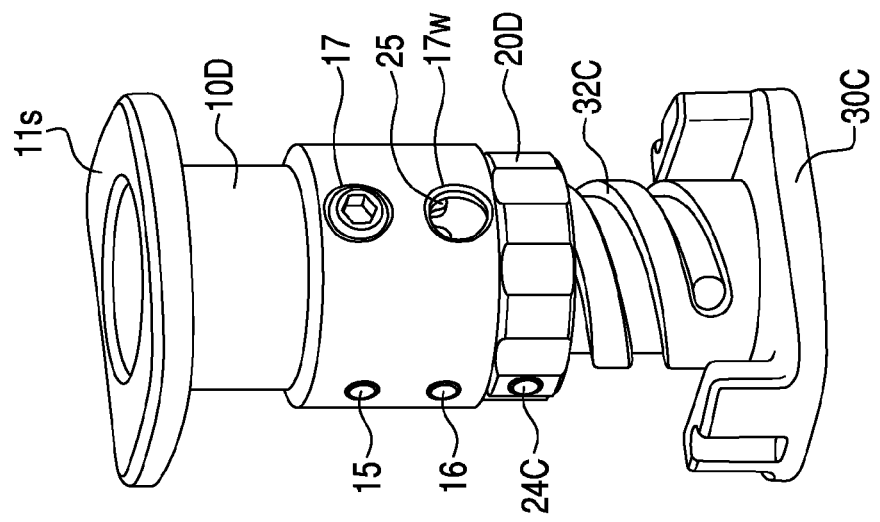
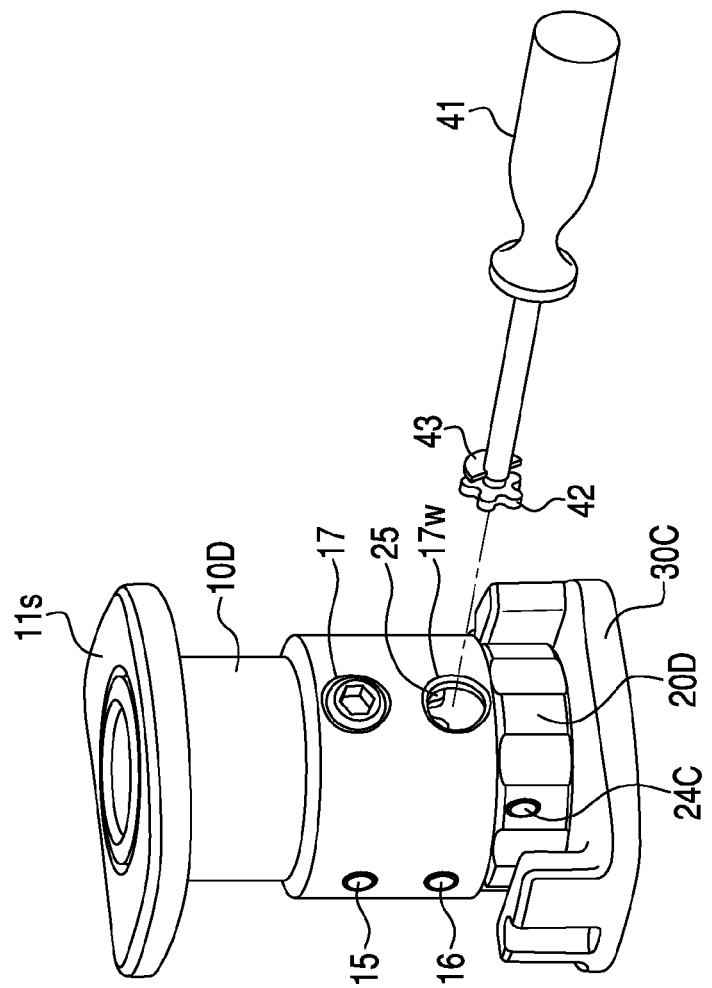
Fig. 13A
Fig. 13B

PROSTHESIS, SYSTEM AND METHOD

BACKGROUND

1. Field

The presently disclosed subject matter relates generally to devices, systems and methods used to replace and/or support a portion of a skeletal structure, and more particularly to devices, systems and methods used to support the spine after removal of at least a part of a vertebra or vertebrae.

2. Description of the Related Art

When a vertebra is damaged, malformed, or diseased, surgery may be used to replace the vertebra or a portion thereof with a prosthetic device to restore spinal column support. For example, vertebral body replacement is commonly used in the treatment of vertebral fracture, tumor, infection, misconfiguration/deformity or other problems or diseases.

In recent years, several artificial materials and implants have been developed to replace the vertebral body, such as, for example, titanium cages, ceramic, ceramic/glass, plastic or PEEK, and carbon fiber spacers. Various expandable prosthetics or expandable cages have also been developed and used for vertebral body replacement. The expandable prosthetic devices are generally adjustable to the size of the cavity created by various procedures, such as a corpectomy procedure. The prosthetic devices are also typically at least partially hollow to accommodate bone cement, bone infusion materials, bone fragments, or other regenerative material to facilitate fusion in vivo. Some expandable prostheses may be adjusted prior to insertion into the cavity, while others may be adjusted in situ. An expandable prosthetic device that is adjustable in situ can provide an optimal, tight fit by in vivo expansion of the device. Some other benefits offered by an expandable prosthetic device are that they can facilitate distraction across the resected vertebra, and allow immediate load bearing after corpectomy.

Instrumentation and specialized tools for insertion of a vertebral implant is one important design parameter to consider when designing a vertebral prosthesis. Spinal surgery procedures can present several challenges because of the small clearances around the prosthetic when it is being inserted into position. Another important design consideration includes the ability of the device to accommodate various surgical approaches for insertion of the vertebral implant.

Techniques, instrumentation and implants have changed over the years and have been better adapted to address many forms of spinal injury and deformities that can occur due to trauma, disease or congenital effects. One type of spinal deformity, a kyphosis, involves a prolapse of the vertebral column towards the front of the body, often caused by the destruction of the vertebral body itself. This destruction can be in the form of a trauma type injury, such as a fracture or burst injury to the vertebral body, or a non-traumatic deformity caused by a tumor or a degeneration of the bone in the vertebral body.

Treatment of a kyphosis in the thoracic or lumbar spine appears now to be best achieved through an anterior approach, particularly in order to avoid some of the more severe complications associated with support or replacement of a damaged vertebral body. In most treatments of a kyphosis, a high degree of anterior reconstruction of the spine is required, most frequently involving total removal of the damaged vertebral body. In a typical anterior approach, partial or total ablation of the vertebral body and the two adjacent vertebral disks is carried out. The remaining space is then distracted to manipulate the spine to its correct orientation.

In some cases, the remaining space is filled with a polymerizable paste or a bone graft which is frequently modeled to give it the shape of the destroyed vertebral body. Frequently, autologous bone, such as that extracted from the ilium, is used to bridge the remaining space. The polymerizable paste can include a PMMA bone cement. Once the space remaining after the removal of the original vertebral body has been filled, an osteosynthesis instrument is positioned between the adjacent unaffected vertebrae to prevent any relative movement therebetween. The osteosynthesis device restabilizes the vertebral column, to support the loads to which the thoracic or lumbar spine is exposed, and to enhance the likelihood and quickness of union of the bone graft material with the adjacent vertebral bodies. Once the bone graft and material is sufficiently solid, the osteosynthesis device normally is not burdened with carrying the primary loading forces or enduring the primary mechanical stresses.

Another variety of implant devices particularly suited for replacement of vertebral bodies include components of generally solid construction which completely occupy the empty vertebral space. Such implants include vertebral prosthesis which include some feature for expansion of the device in situ.

In recent years, the application of anterior approaches to instrumenting the spine has become more prevalent. As these anterior approaches advance, vertebral body replacements that are specifically designed to enjoy all of the benefits of anterior surgery.

SUMMARY

Some of the related art devices do not provide means for osteosynthesis between the intact vertebrae. These devices lack features that can either permit bone ingrowth or facilitate placement of bone graft between adjacent healthy vertebrae. However, it is generally recognized that a more permanent and stable correction of a skeletal, and particularly a spinal, issue occurs with fusion of a bony mass in place of the replaced bone or vertebra. Other bone and vertebral prosthesis devices offer no means for adjusting the size of the implant to accommodate the specific vertebral anatomy. Further, other of the devices do not contemplate some auxiliary fixation to help provide a stable construct. In addition, many related art devices have not been able to provide a dynamic loading type structure that is also compact in size and that allows for bone ingrowth and in situ expansion.

Accordingly, it may be beneficial to provide a prosthesis that is height adjustable by rotation or other movement of an intermediary structure located between a top structure and a bottom structure. In addition, it may be beneficial to provide an implant that includes a spring or otherwise biased structure to allow a dynamic type of loading, while the spring structure also serves as a guide for specific movement between the different structural components of the implant in order to ensure a compact nature for the implant. It may also be beneficial to use a combination of pins and grooves in different configurations to allow for quick and easy manipulation of the different structural components of the implant to minimize the structural components while simultaneously permitting smooth and consistent movement between the structural components relative to each other.

According to one aspect of the disclosed subject matter, an implant includes a spring formed at the base of a bottom structure. The spring can include two diametrically opposed helical/spiral slots that receive a bottom pin associated with both the bottom structure and an intermediary structure. The bottom structure can also have a longitudinal slot to receive a top pin associated with both the bottom structure and a top structure. The height of the vertebral body replacement implant can be variable. The implant can be adjusted to a desired intermediate position by rotating the intermediary structure (e.g., a nut shaped structure) by means of a wrench, for example. During expansion, the bottom pin associated with the intermediary and bottom structures slides along the pathway of the two helical slots. Another set of rotational pins (associated with the top structure and intermediary structure) stay inside a groove in the intermediary structure as the intermediary structure rotates, and the top pin slides in the longitudinal slot (one translational degree of freedom). A set screw can lock/fix the device at a desired height. The function of the pins, the groove in the intermediary structure, and the longitudinal slot in the bottom structure is to convert rotational motion of the intermediary structure into translational motion of the top structure (relative to the bottom structure). Therefore, the rotational orientation of the top structure with respect to bottom structure is unchanged during expansion. This allows for the design of an anatomically optimum endplate geometry for the device. The spring in the bottom structure can be designed with different stiffnesses to accommodate different patient or user needs.

According to one aspect of the disclosure, an implant device configured to be inserted between adjacent skeletal components can include a top structure including a top bone facing surface, a bottom structure including a bottom bone facing surface substantially opposed to the top bone facing surface, and an intermediary structure configured to be rotatable with respect to the bottom structure and about a central axis. The bottom structure can include a first guide structure and a second guide structure. The first guide structure can be configured to guide the intermediary structure in both a rotational direction about the central axis and an axial linear direction along the central axis when the intermediary structure is rotated. The second guide structure can be configured to guide the top structure in the axial linear direction along the central axis when the intermediary structure is rotated.

According to another aspect of the disclosed subject matter, an implant device configured to be inserted between adjacent skeletal components can include a top structure including a top bone facing surface, a bottom structure including a bottom bone facing surface substantially opposed to the top bone facing surface and located at a first end of the bottom structure, an opposing surface opposed to the bottom bone facing surface and located at a second end of the bottom structure opposed to the first end, a helical groove structure located between the bottom bone facing surface and the opposing surface of the bottom structure and about a central axis of the bottom structure, and an intermediary structure including at least one pin extending from the intermediary structure and into the helical groove structure such that, when the intermediary structure is rotated with respect to the bottom structure, the pin and the helical groove structure guide the intermediary structure to move in both a rotational direction about the central axis and in an axial linear direction along the central axis.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 2A is a perspective view of the implant of FIG. 1 in a non-extended position.

FIG. 2B is a perspective view of the implant of FIG. 1 in a fully-extended position.

FIG. 3 is a perspective view of a bottom structure of the implant of FIG. 1 including a pin from the top structure and a pin from the intermediary structure.

FIG. 4 is a perspective view of an intermediary structure of the implant of FIG. 1.

FIG. 5 is a perspective and partially transparent view of the implant of FIG. 1 in a fully-extended position.

FIG. 7A is a perspective view of the implant of FIG. 6 in a fully-extended position.

FIG. 7B is a perspective view of the implant of FIG. 6 in a non-extended position.

FIG. 10A is a perspective view of the implant of FIG. 9 in a non-extended position.

FIG. 10B is a perspective view of the implant of FIG. 9 in a fully-extended position.

FIG. 13A is a perspective view of the implant of FIG. 12 in a non-extended position.

FIG. 13B is a perspective view of the implant of FIG. 12 in a fully-extended position.

DETAILED DESCRIPTION OF EXEMPLARY EMBODIMENTS

Figure 1:
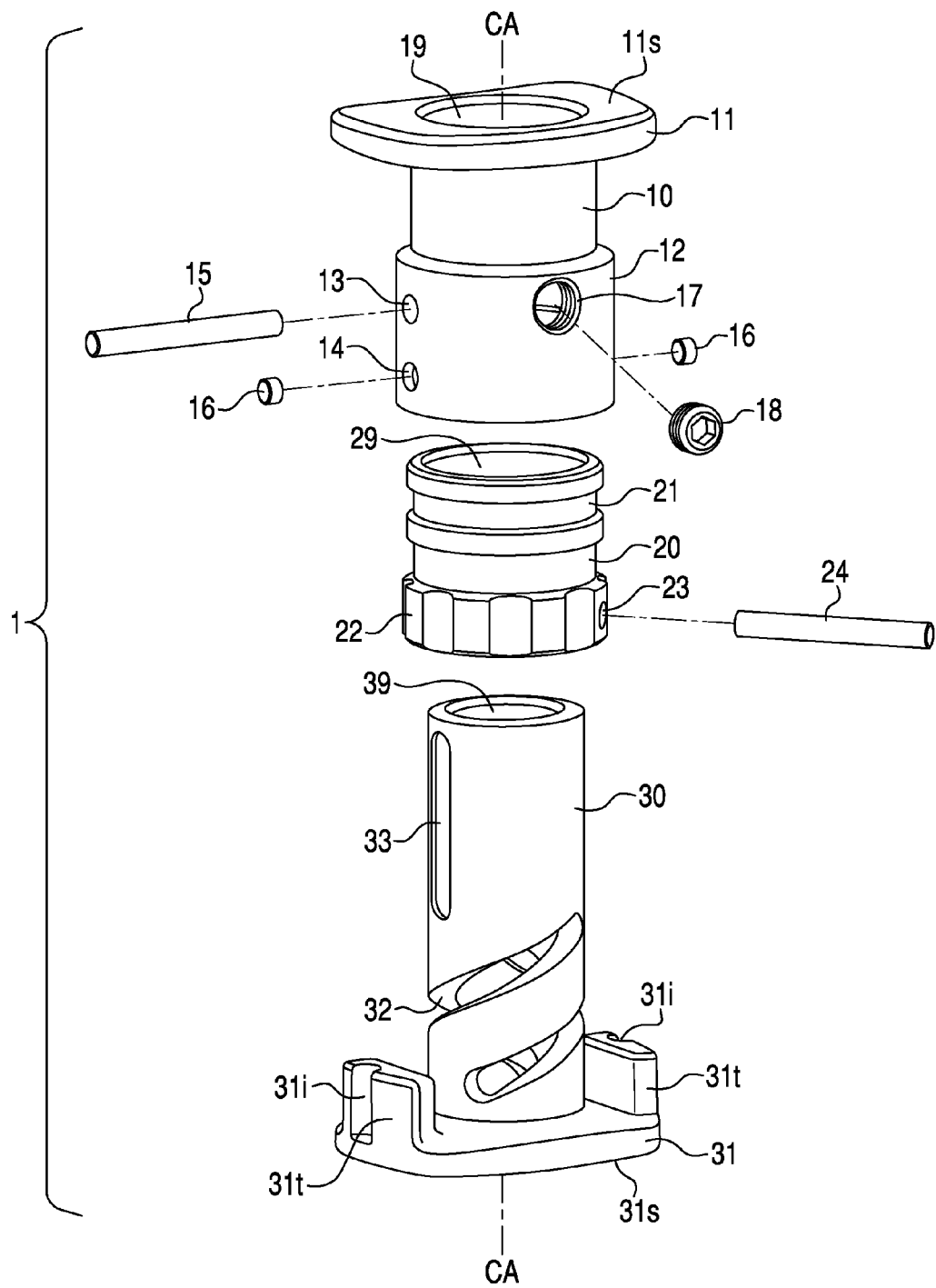
FIG. 1 is a perspective exploded view of an implant device made in accordance with principles of the disclosed subject matter.

FIG. 1 is a perspective exploded view of an implant device 1 made in accordance with principles of the disclosed subject matter. The implant device 1 can include a top structure 10, an intermediary structure 20, and a bottom structure 30. Each of the structures 10, 10B-D (10), 20, 20B-D (20), and 30, 30B, 30C (30) can be configured to cooperate with each other and mate with each other such that relative movement of one structure can cause movement in other of the structure(s). In particular, in one embodiment, rotational movement of the intermediary structure 20 can cause the implant 1 to expand (or contract, depending on direction of rotation of the intermediary structure 20) along a central axis of the implant 1. In addition, each of the structures 10, 20, and 30 can include a central opening 19, 29, and 39, respectively. The central openings 19, 29, and 39 can be aligned such that the implant 1 takes on a tubular configuration in which an interior space can be employed to carry certain materials that may be beneficial to the medical procedure, including bone regeneration materials, bone fragments, pharmaceuticals, cements, combinations of these materials, etc.

The top structure 10 can be configured as a tubular structure having a central opening 19 running along a central axis CA of the implant 1. A first end of the top structure 10 can include a bone facing collar 11 that has a bone facing surface 11s configured to face bone and/or tissue to which the implant is to be connected during implantation. A narrower tubular structure extends between the bone facing collar 11 and opposing collar 12. The opposing collar 12 can be located at an end of the top structure 10 along the central axis CA that is opposed to the bone facing collar 11. In addition, the opposing collar 12 can be enlarged as compared to the adjacent tubular portion such that the opposing collar 12 can accommodate and seat the top portion of the intermediary structure 20 therein.

A pin 15 can be located in a pin accessway 13 in the opposing collar 12. The pin 15 can extend across the entire central opening 19 in the top structure 10 and attach to or be supported at accessways 13 located in opposing wall surfaces of collar 12. The pin 15 can also be located within a second guide structure, such as slot 33 of the bottom structure 30, when the implant 1 is finally assembled. In addition, a second pin 16 can be provided in two parts and located in accessway 14 just below the pin 15 in the top structure 10. Pin 16 can extend from an interior surface of opposing wall surfaces within the central opening 19 of the top structure 10 and terminate before crossing the halfway mark between opposing walls within the top structure 10. In addition, both pins 15 and 16 can extend into the top structure in a direction that is substantially (i.e., almost or exactly) perpendicular to the central axis 19 of the top structure 10. Pin 16 can also be located within a channel 21 of the intermediary structure 20 when the implant 1 is finally assembled.

The intermediary structure 20 of this embodiment is configured to rotate with respect to at least one of the top structure 10 and the bottom structure 30. As indicated above, an annular channel 21 can be provided in a top portion of the intermediary structure 20 to provide a race or guideway for pin 16 of the top structure 10. The pin 16 and channel 21 serve to guide rotation of the top structure relative to the intermediary structure 20 while preventing axial or linear movement therebetween along a direction parallel with the central axis CA of the implant 1. The intermediary structure 20 can include a plurality of knurls 22 that assist a user in rotating the intermediary structure 20 relative to the top structure 10 and bottom structure 30. A pin accessway 23 can be placed in the area of the knurls 22 and can contain a pin 24 therein. The pin 24 can be located in a first guide structure, such as helical groove 32, in the bottom structure 30 when the implant 1 is finally assembled.

The bottom structure 30 can include the first guide structure configured to guide the intermediary structure 20 simultaneously in both a rotational direction about the central axis CA and an axial linear direction along the central axis CA when the intermediary structure 20 is rotated. For example, the helical groove 32 can be provided as the first guide structure. The bottom structure 30 can also include a second guide structure configured to guide the top structure 10 in the axial linear direction along the central axis CA when the intermediary structure 20 is rotated. For example, a linear groove 33 can be provided as the second guide structure. The bottom structure 30 can also include a bottom bone facing collar 31 with a bone facing surface 31s that is configured to face bone and/or tissue to which the implant is to be connected during implantation. In this embodiment, the bone facing surface 31s is generally opposed to the bone facing surface 11 of the top structure 10, and therefore the bone facing surface 11 and bone facing collar 31 are contained in planes that are substantially parallel with each other (and substantially perpendicular to the central axis). Of course, it is contemplated that these surfaces can be angled with respect to each other and/or with respect to the central axis for various applications or user preferences.

The bottom structure 30 can include tabs 31t that extend back towards a central portion of the implant 1 from outer peripheral edges of the bone facing collar 31. Indents 31i can be located in each of the tabs 31t to facilitate connection of the bottom structure 30 to a target structure, such as a bone, tissue, test bench or other object for attachment through the use of separate attachment structure(s). For example, a clamp, camming device, or a screw head can be located in indent 31i to lock the bottom structure 30 to a target structure.

FIGS. 2A and B are perspective views of the implant 1 in a non-extended position and a fully-extended position, respectively. After being located in a desired position, the implant 1 can be expanded to secure itself in place and provide a correct sizing for a given procedure by rotating the intermediary structure 20 with respect to the top structure 10 and bottom structure 30 of the implant 1. For example, when the intermediary structure 20 is rotated counterclockwise (as viewed from above the top structure 10 along the central axis CA), the top structure 10 will move away from the bottom structure 30 along the central axis CA, thereby expanding the overall length of the implant 1 to fit within a desired location.

FIGS. 3-5 depict the various components that permit the relative movement between the top structure 10, intermediary structure 20, and bottom structure 30. In particular, the pin 15 that extends between interior surfaces of the central opening 19 in the top structure can also be located within the linear groove 33 in the bottom structure 30. This configuration permits the pin 15 to travel only in a direction dictated by the shape of the groove 33 which, in this exemplary embodiment, is a linear and vertical directional shape that is substantially parallel with the central axis CA of the implant 1. The pin 15 can be press-fit into the accessway 13 in the top structure 10 and locked with respect to the top structure at least with respect to a translational or linear motion component. Connection between the pins and corresponding structures (either top structure 10 or intermediary structure 20) can be a press-fit connection. However, other connection structures and systems are contemplated, including a shrink fit connection which can be used if the corresponding structures are made out of metal (Ti, CoCr, etc.). Other alternative connections may include adhesive bonding, welding, or a threaded connection etc. Although not shown, it is conceivable that the pin 15 could be rotatable within accessway 13 and with respect to the top structure 10). The linear groove 33 through its guiding action on pin 15 restrains movement of the top structure 10 to a linear motion along the central axis CA with respect to the bottom structure 30 (and with respect to the intermediary structure 20).

While pin 15 guarantees only linear motion between the top structure 10 and the bottom structure 30, pin 16 effectively constrains the relative motion between the top structure 10 and the intermediary structure 20 to be only rotational in nature. In particular, the pin 16 can be a two part structure that extends from two part accessway 14 located on either side of the interior surface of the central opening CA in the top structure 10. The pin 16 can extend from the interior surface of the top structure 10 and be located within the annular channel 21 in the intermediary structure 20. This configuration permits the pin 16 to travel only in a direction dictated by the shape of the channel 21 which, in this exemplary embodiment, is shaped as an annular ring located about a top periphery of the intermediary structure 20 with the central axis CA as its center. Opposing portions of the pin 16 can be friction fit into respective portions of the accessway 14 in top structure 10 and locked with respect to the top structure 10, at least with respect to a translational or linear motion component (the pin 16 could be rotatable within accessway 14 about its own central axis). Thus, the channel 21 through its guiding action on pin 16 restrains movement of the top structure 10 to a rotational motion about the central axis CA with respect to the intermediary structure 20.

Pin 24, which is located in the intermediary structure 20, can also be located within, and cooperate with, the first guide structure to allow the intermediary structure 20 to rotate and translate at the same time with respect to the bottom structure 30 when a force is applied to the intermediary structure 20. In the embodiment shown, the first guide structure can include a pair of helical grooves 32 that extend entirely from an exterior surface through an interior surface of a tubular portion of the bottom structure 30 to form a type of dynamic spring that will provide load damping characteristics to the implant 1 as well as provide guidance to the pin 24. Specifically, the helical grooves 32 allow the implant 1 to elastically compress in a direction along the central axis when a loading force is applied thereto, while returning to the original length and configuration when the loading force is removed. The loading force can occur due to normal movement of a patient after implantation. The dynamic nature of the spring structure formed by helical grooves 32 can provide various benefits, including increased stress and strain components on materials located within the implant 1 which can act as a catalyst for bone growth regeneration, as well as increased prevention of fracture or deterioration of the implant 1 itself due to vibration, force and shock damping characteristics of the spring structure.

The relative motion between the bottom structure 30 and the intermediary structure 20 can be defined by the configuration of the helical grooves 32 and pin 24. In particular, the pin 24 can be a single structure that extends from either side of an interior surface of the central opening 29 in the intermediary structure 20. The portion of the pin 24 located within the central opening 29 can be located within the helical grooves 32 in the bottom structure 30. This configuration permits the pin 24 to travel only in a direction dictated by the shape of the helical grooves 32 which, in this exemplary embodiment, is shaped as an annular helical groove that rotates about the central axis CA of the implant 1. Opposing portions of the pin 24 can be press-fit into respective portions of the accessway 23 in intermediary structure 20 and locked with respect to the intermediary structure, at least with respect to a translational or linear motion component (the pin 24 could be stationary and fixed or could be rotatable within accessway 23 and with respect to the intermediary structure 20). Thus, the helical grooves 32, through their guiding action on pin 24, restrain movement of the intermediary structure 20 to a specific combined rotational and translational motion about and along the central axis CA with respect to the bottom structure 30.

As described above, the top structure 10 can be limited to linear motion with respect to the bottom structure 30 by the interaction of pin 15 with the second guide structure (e.g., channel 33) of the bottom structure 30. Thus, when the intermediary structure 20 is rotated, the first guide structure of the bottom structure 30 causes the intermediary structure 20 to simultaneously move in a linear direction parallel with and along the central axis CA of the implant 1. The linear motion of the intermediary structure 20 is transferred to the top structure 10 via the pin 16 and channel 21 connection, while the rotational component of motion is "lost" on the top structure 10 by virtue of the connective structure: the pin 16 rotating within channel 21 allows the intermediary structure 20 to rotate with respect to the top structure 10 (the top structure 10 does not rotate). Only the linear component of the motion of the intermediary structure 20 is thus transferred to the top structure 10.

A set screw threaded accessway 17 and set screw 18 can be located in the collar 12 of the top structure 10. When the top structure 10 is located at a desired position with respect to the bottom structure 30, the set screw 18 can be rotated within the threaded accessway 17 to abut against an exterior surface of the bottom structure 30 and thereby lock the bottom structure 30 and top structure 10 together (with respect to both rotational and translational freedom). Thus, after the implant 1 is located correctly in a target area, and after the intermediary structure 20 is rotated to extend the implant 1 to a correct length, the set screw 18 can be turned to lock in the length of the implant 1 and to prevent linear motion between top structure 10 and bottom structure 30 and/or rotational motion between intermediary structure 20 and the top structure 10 or bottom structure 30.

Figure 6:
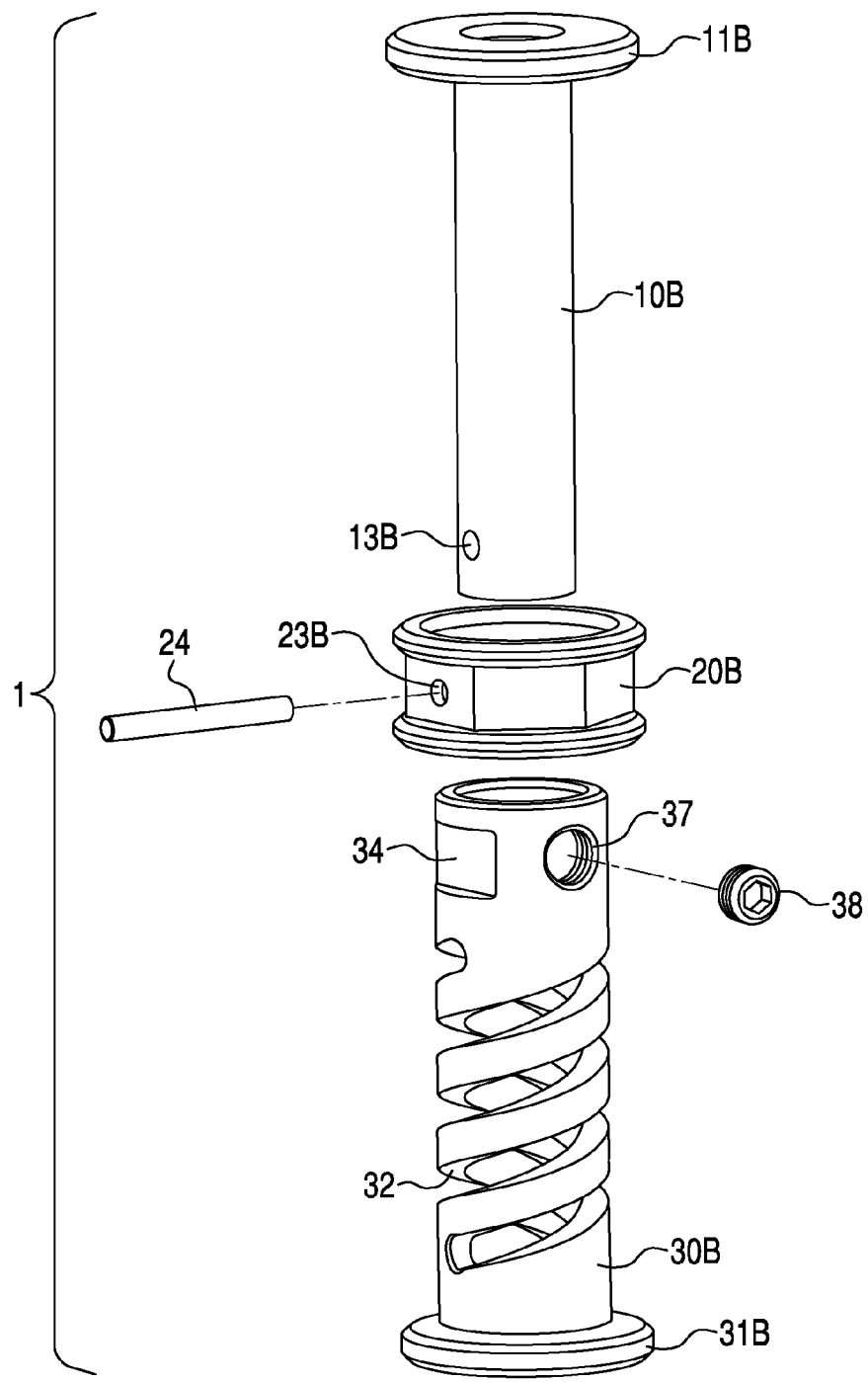
FIG. 6 is a perspective exploded view of another embodiment of an implant device made in accordance with principles of the disclosed subject matter.

FIG. 6 is a perspective exploded view of another embodiment of an implant device made in accordance with principles of the disclosed subject matter. In this embodiment, the intermediary structure 20B is shaped as an annular collar with outer polygonal faces (for connection to a wrench or the like for rotation) and includes a single pin 24 located in an accessway 23B and extending across the central opening of the intermediary structure 20B. The pin 24 can be located within the helical grooves 32 located in the bottom structure 30 and a pin accessway 13B located on the top structure 10B. The pin 24 locks the top structure 10B and intermediary structure 20B together such that they are guided to move and/or rotate simultaneously and together with respect to the bottom structure 30B. Thus, when the intermediary structure 20B is rotated by a user, both the intermediary structure 20B and top structure 10B simultaneously rotate and translate with respect to the bottom structure 30B.

In this embodiment, the top structure 10B includes a bone facing collar 11B that is configured as a circular disk, and the bottom structure 30B includes a bone facing collar 31B also configured as a circular disk. The circular shape of the bone facing collars 11B and 31B allow the relative rotational orientation between the bone facing collars 11B and 31B to be somewhat irrelevant. In other words, when the top structure 10 rotates relative to the bottom structure 30 as described above (when rotational force is applied to the intermediary structure 20), the general shape of the bone facing collar 11B, 31B that is presented to the bone, tissue or other target attachment material/structure located at either end of the implant 1 will be the same due to the symmetry of the disk shaped bone collars 11B, 31B.

A set screw threaded accessway 37 and set screw 38 can be located at a top portion of the bottom structure 30B. When the top structure 10B is located at a desired position with respect to the bottom structure 30B, the set screw 38 can be rotated within the threaded accessway 37 to abut against an exterior of the top structure 10 and thereby lock the bottom structure 30 and top structure 10 together (with respect to both rotational and translational freedom). Diametrically opposed flats 34 can also be provided in a top exterior surface of the bottom structure 30B to allow an implant inserter to hold/grip an implant device.

Figure 8:
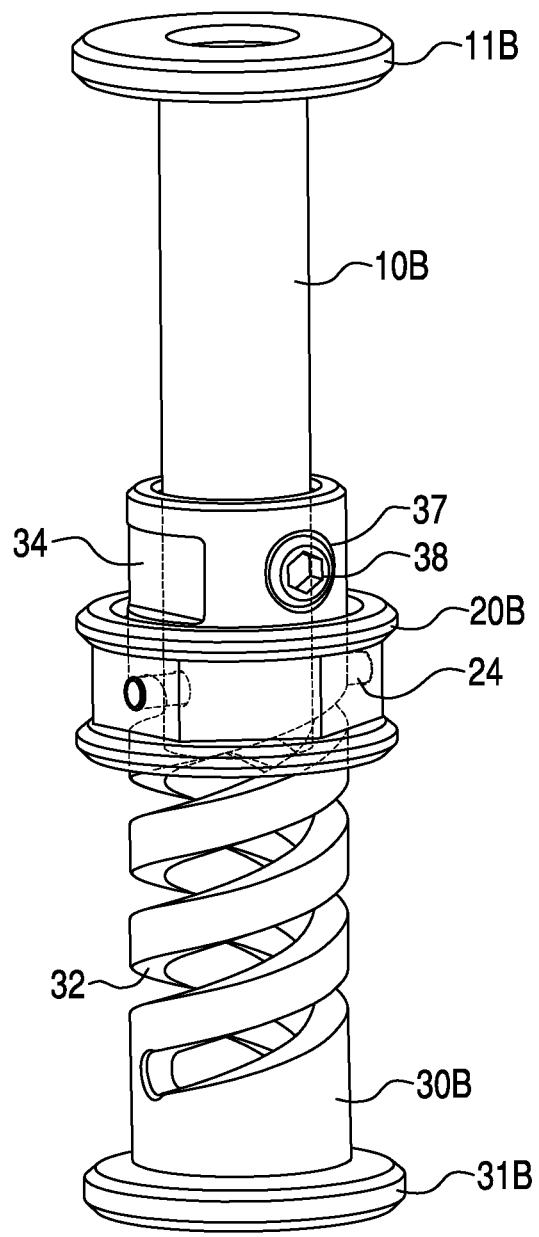
FIG. 8 is a perspective and partially transparent view of the implant of FIG. 6 in a fully-extended position.

FIGS. 7A and B are perspective views of the implant of FIG. 6 in a fully-extended position and a non-extended position, respectively. FIG. 8 is a perspective and partially transparent view of the implant in a fully-extended position. The exemplary embodiment of the implant 1 shown in FIGS. 6-8 operates via rotation of the intermediary structure 20B. Once the implant is located in a target area, the implant can be expanded by rotating the intermediary structure 20B. The rotation of the intermediary structure also causes the top structure 10B to rotate due to the interconnected nature of the top and intermediate structures 10B and 20B (pin 24 extends through accessway openings in each of the top structure 10B and intermediary structure 20B to lock the structures together). The pin 24 also resides in the helical grooves 32 of the bottom structure 30B when assembled, and therefore guides both the top structure 10B and intermediary structure 20B in both rotating and linear direction components parallel with and about the central axis CA.

Once the implant 1 is in place, the top structure 10B, intermediary structure 20B, and bottom structure 30B can all be locked with respect to each other by use of the set screw 38 as described above. The helical grooves 32 in this embodiment then serve as a spring component to dampen the force distributed between the tissues or bones to which the device is attached. For example, when the device is placed between vertebrae in a spine, the implant will dampen force that translates along the longitudinal axis of the spine. Thus, the implant 1 can provide more natural spinal movement to the host or recipient and may provide for quicker and easier recovery from an implantation or other related medical procedure. In addition, as noted above, the relative movement due to the spring action can initiate quicker and stronger tissue or bone regeneration in the area of the implant 1.

Figure 9:
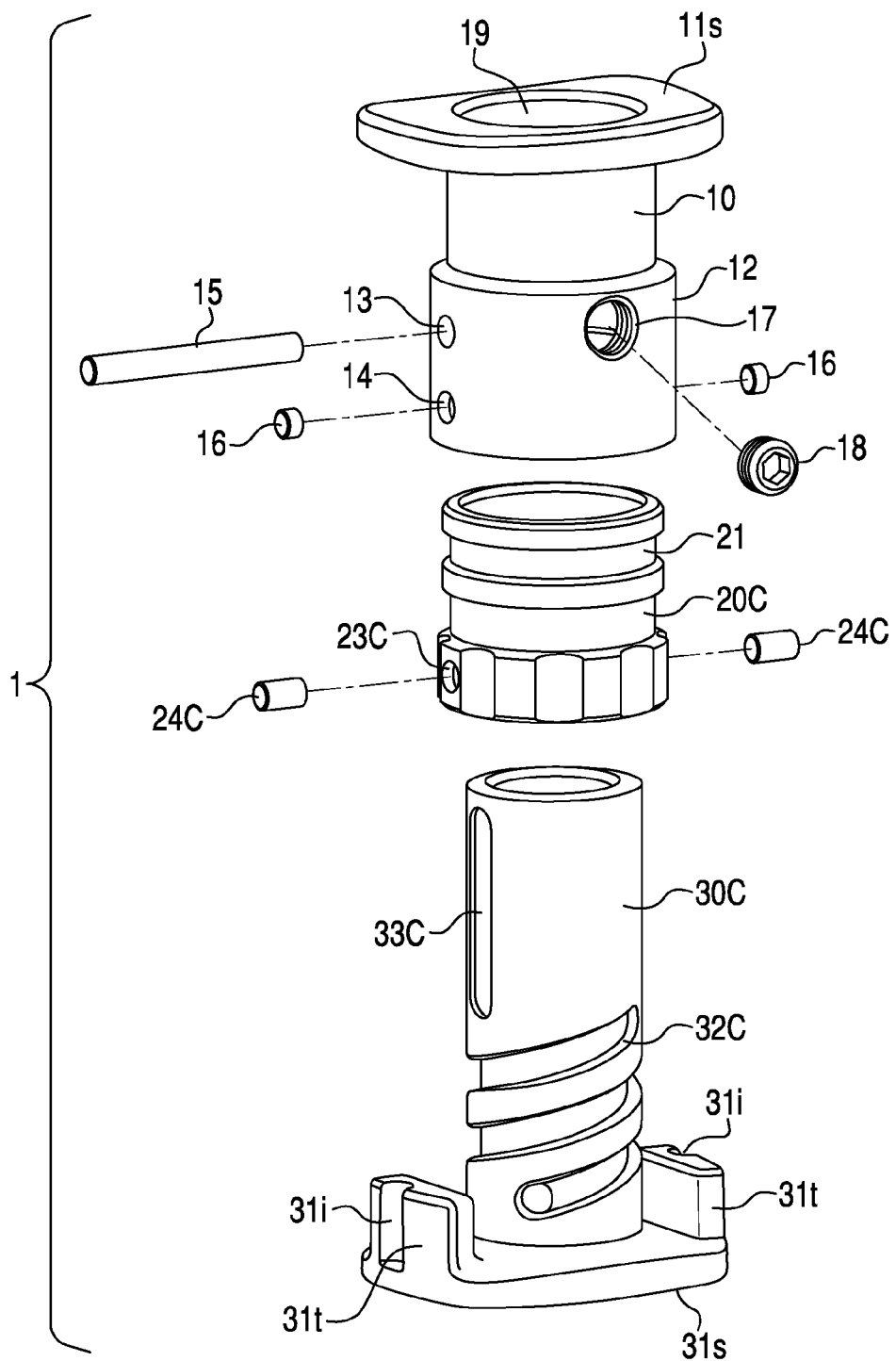
FIG. 9 is a perspective exploded view of another embodiment of an implant device made in accordance with principles of the disclosed subject matter.

FIG. 9 is a perspective exploded view of another embodiment of an implant device made in accordance with principles of the disclosed subject matter. This embodiment of the implant 1 can be constructed similar to the embodiment shown in FIG. 1. However, in this embodiment, helical grooves 32C are formed such that they do not extend fully through the side walls of the bottom structure 30C. Specifically, grooves 32C are formed as channel type structures that extend partially through the side wall from an exterior surface towards (but not entirely through) an interior surface of the side wall of the bottom structure 30C. Thus, the bottom structure 30C of this embodiment is a solid structure that does not exhibit the spring damping characteristics as described above with regard to the embodiments of FIG. 1 and FIG. 6.

Figure 11:
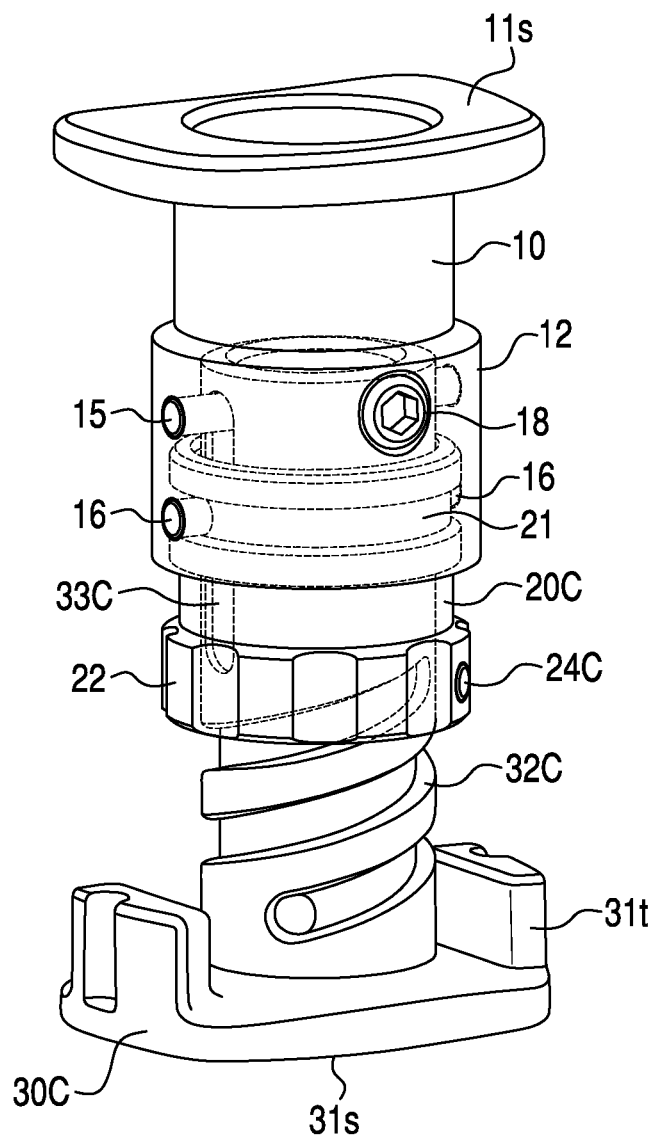
FIG. 11 is a perspective and partially transparent view of the implant of FIG. 9 in a fully-extended position.

FIGS. 10A and B are perspective views of the implant of FIG. 9 in a non-extended and fully-extended position, respectively, while FIG. 11 is a perspective and partially transparent view of the implant of FIG. 9 in a fully-extended position. With respect to the implantation and extension operation, this embodiment can function similar to that of the embodiment of FIG. 1. Specifically, the pin 15 that extends between interior surfaces of the central opening 19 in the top structure can also be located within the linear groove 33C in the bottom structure 30C. This configuration permits the pin 15 to travel only in a direction dictated by the shape of the groove 33C which, in this exemplary embodiment, is a linear and vertical directional shape that is substantially parallel with the central axis CA of the implant 1. Alternatively, the pin 15 can be a two part structure and the groove 33C can be a channel that does not extend all the way through the side wall of the bottom structure 30C (such that the pin 15 cannot extend entirely across the central opening 19). The pin 15 can be press-fit into the accessway 13 in top structure 10 and locked with respect to the top structure at least with respect to a translational or linear motion component (the pin 15 could be stationary and fixed, or rotatable within accessway 13 and with respect to the top structure 10). Thus, the linear groove 33C through its guiding action on pin 15 restrains movement of the top structure 10 to a linear motion along the central axis CA with respect to the bottom structure 30C (and with respect to the intermediary structure 20C).

While pin 15 allows only linear motion between the top structure 10 and the bottom structure 30C, pin 16 effectively constrains the relative motion between the top structure 10 and the intermediary structure 20C to be rotational in nature. In particular, the pin 16 can be a two part structure that extends from two part accessway 14 located on either side of the interior surface of the central opening CA in the top structure 10. The pin 16 can extend from the interior surface of the top structure 10 and be located within the annular channel 21 in the intermediary structure 20C. This configuration permits the pin 16 to travel only in a direction dictated by the shape of the channel 21 which, in this exemplary embodiment, is shaped as an annular ring located about a top periphery of the intermediary structure 20C with the central axis CA as its center. Opposing portions of the pin 16 can be press-fit into respective portions of the accessway 14 in top structure 10 and locked with respect to the top structure, at least with respect to a translational or linear motion component (the pin 16 could be stationary and fixed, or rotatable within accessway 14 about the central axis CA and with respect to the top structure 10 about an axis of the pin itself). Thus, the channel 21 through its guiding action on pin 16 restrains movement of the top structure 10 to a rotational motion about the central axis CA with respect to the intermediary structure 20C.

Pin 24C located in the intermediary structure 20C can also be located within, and cooperate with, the first guide structure to allow the intermediary structure 20C to rotate and translate at the same time with respect to the bottom structure 30C when a force is applied to the intermediary structure 20C. In the embodiment shown, the first guide structure is a pair of helical grooves 32C that extend only partially from an exterior surface towards an interior surface of a tubular portion of the bottom structure 30C to provide guidance to the pin 24C. Unlike the embodiment of FIGS. 1-8, the helical grooves 32C do not allow the implant 1 to substantially elastically compress in a direction along the central axis when a loading force is applied thereto. Thus, the implant 1 will provide a different stress and strain profile to the host or user, and may beneficially be applied in certain circumstances.

The relative motion between the bottom structure 30C and the intermediary structure 20C can be defined by the configuration of the helical grooves 32C and pin 24C. In particular, the pin 24C can be a two part structure each extending from either respective side of an interior surface of the central opening 29 in the intermediary structure 20C. The portion of the pin 24C located within the central opening 29 can be located within the helical grooves 32C in the bottom structure 30C. This configuration permits the pin 24C to travel only in a direction dictated by the shape of the helical grooves 32C which, in this exemplary embodiment, is shaped as an annular helical groove that rotates about the central axis CA of the implant 1. Outer most portions of the pin 24C can be press-fit into respective portions of the accessway 23C in the intermediary structure 20C and locked with respect to the intermediary structure, at least with respect to a translational or linear motion component (the pin 24C could be stationary and fixed, or can be rotatable within accessway 23C about its own central axis). Thus, the helical grooves 32C, through their guiding action on pin 24C restrains movement of the intermediary structure 20C to a specific combined rotational and translational motion about and along the central axis CA with respect to the bottom structure 30C.

As described above, the top structure 10 can be limited to linear motion with respect to the bottom structure 30C by the interaction of pin 15 with the second guide structure (e.g., channel 33C) of the bottom structure 30C. Thus, when the intermediary structure 20C is rotated, the first guide structure of the bottom structure 30C causes the intermediary structure 20C to simultaneously rotate and move in a linear direction parallel with and along the central axis CA of the implant 1. The linear motion of the intermediary structure 20C is transferred to the top structure 10 via the pin 16 and channel 21 connection, while the rotational component of motion is "lost" on the top structure 10 by virtue of the connective structure: the pin 16 rotating within channel 21 allows the intermediary structure 20C to rotate with respect to the top structure 10 (the top structure 10 does not rotate relative to the bottom structure 30C). Only the linear component of the motion of the intermediary structure 20C is thus transferred to the top structure 10.

A set screw threaded accessway 17 and set screw 18 can be located in the collar 12 of the top structure 10. When the top structure 10 is located at a desired position with respect to the bottom structure 30C, the set screw 18 can be rotated into the threaded accessway 17 to abut against an exterior surface of the bottom structure 30C and thereby lock the bottom structure 30C and top structure 10 together (with respect to both rotational and translational freedom). Thus, after the implant 1 is located correctly in a target area, and after the intermediary structure 20C is rotated to extend the implant 1 to a correct length, the set screw 18 can be turned to lock in the length of the implant 1 and to prevent linear motion between top structure 10 and bottom structure 30C and/or rotational motion between intermediary structure 20C and the top structure 10 or bottom structure 30C.

Figure 12:
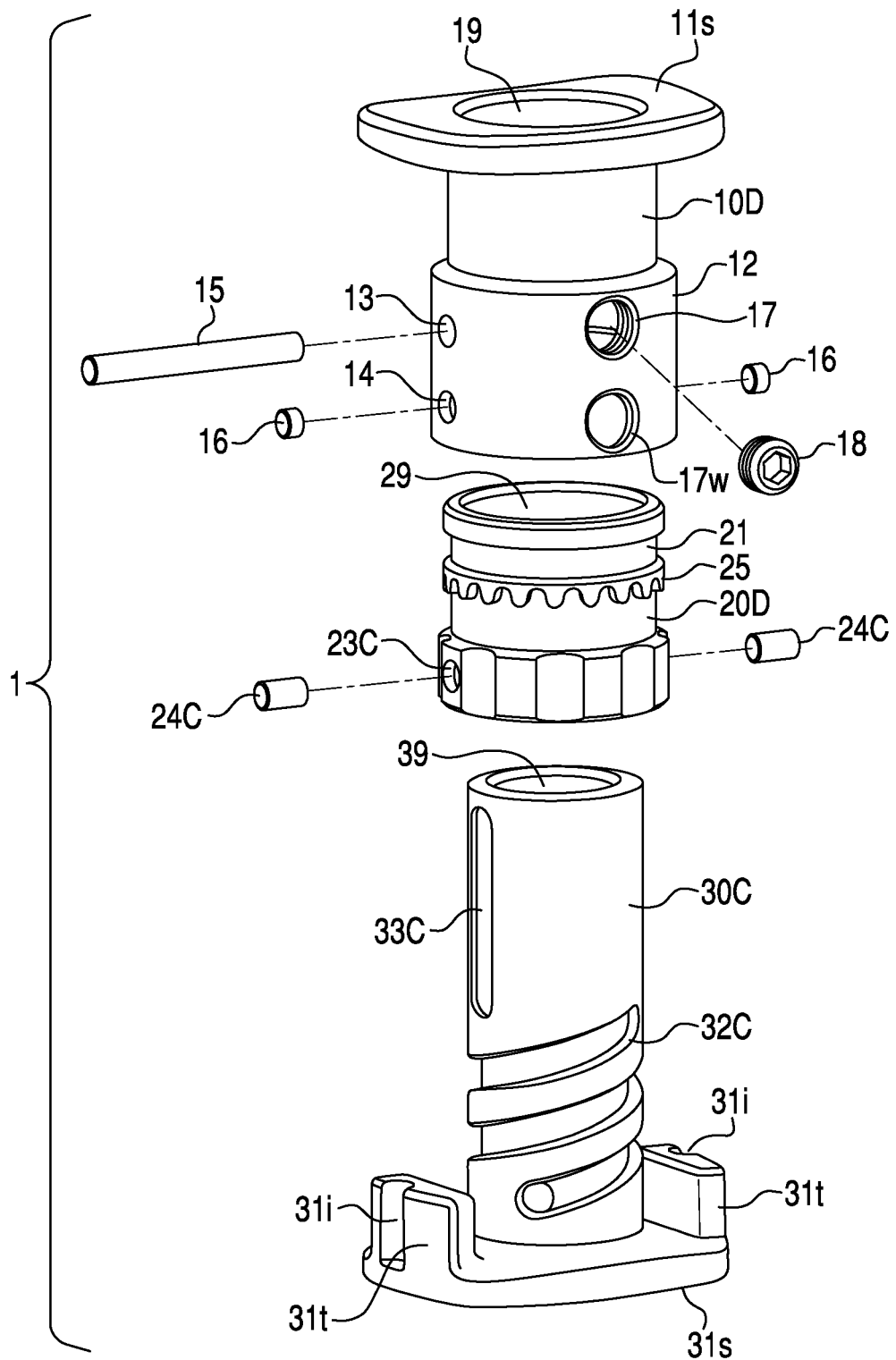
FIG. 12 is a perspective exploded view of another embodiment of an implant device made in accordance with principles of the disclosed subject matter.

FIG. 12 is a perspective exploded view of another embodiment of an implant device made in accordance with principles of the disclosed subject matter. FIGS. 13A and B are perspective views of the implant of FIG. 12 in a non-extended position and fully-extended position, respectively. This embodiment can be similar to the embodiment described above with respect to FIGS. 9-11, with an additional feature in that the intermediary structure 20D and top structure 10D can include an additional motion structure to assist in applying rotational force to the intermediary structure 20D. In particular, the top structure 10D can include a window 17W located just below the accessway 17 for set screw 18. The window 17W can be formed in various shapes and can be located in other locations. In the particular embodiment shown, the window 17W is formed as a circular through-hole in the side surface of collar 12 in the top structure 10D.

In addition to the window 17W, the motion structure can include a plurality of gear teeth 25 located about a periphery of an exterior annular surface of the intermediary structure 20D. Thus, the gear teeth 25 can be visible and accessed through the window 17W when the implant 1 is assembled. As shown in FIG. 13A, the implant 1 can be part of a system that includes a tool 41 designed to be inserted into window 17W to motivate gears 25. Specifically, the tool 41 can include a mating gear 42 at a distal end and a collar 43 located adjacent the gear and rotatably supported with respect to a shaft to which the gear 42 is attached. Accordingly, when a user desires to apply a rotational force to the intermediary structure, the user can insert the distal end of tool 41 into window 17W until teeth of gear 42 mate with gear teeth 25 of the intermediary structure 20D. Then, the collar 43 can rest and lock onto a similarly (or matingly) shaped portion of the window 17W such that the collar 43 tends to keep the gear teeth 25 in constant contact with the teeth of gear 42. Once the gear 42 and collar 43 are in place, the user can turn the main shaft of the tool by rotating the handle of the tool 41. This rotation causes the intermediary structure 20D to rotate about the central axis CA to thereby extend (or collapse) the implant 1.

While certain embodiments of the invention are described above, it should be understood that the invention can be embodied and configured in many different ways without departing from the spirit and scope of the invention. For example, as explained above, the geometry of each of the top structure 10, 10B-D (10), bottom structure 20, 20B-D (20), and intermediary structure 30, 30B, 30C (30) can vary considerably and remain within the contemplated scope of the present subject matter. For example, the cross sections of each of these structures can be circular, polygonal, symmetrical, non-symmetrical, etc., depending on a particular application and user preferences. In addition, the cross-sectional shapes can vary between each of the structures provided they still either permit or prevent relative movement between each other, as desired. The specific overall shape of the structures 10, 20, 30 can also vary widely in accordance with patient needs or user preference. The shapes can also be predetermined for a specific patient through the use of pre-operative imaging and subsequent computer modeling of each of the structures 10, 20, 30. In particular, the bone facing surfaces 11s and 31s can be shaped according to specific imaging for a patient such that the interface substantially mirrors the bone or other tissue to which it will be attached. The imaging and fabrication of the bone facing (and other) surfaces can be accomplished either prior to the medical procedure or during the medical procedure, depending on preference of the user and/or whether the target bone or tissue for attachment is to be resected or otherwise changed during the medical procedure. It should also be understood that while we describe endplates as bone facing structures, it is contemplated that other types of tissue, attachment mechanisms, adhesive, or prosthetic devices could be located between the bone facing surface and the bone adjacent which the implant 1 is being located, and that may ultimately be stabilized by use of the implant 1.

The material from which each of the top structure 10, bottom structure 20, and intermediary structure 30 is made can vary considerably. For example, each of the structures can be made from stainless steel, titanium, aluminum, alloys, ceramics, carbon fiber, polyether ether ketone (PEEK), other plastics, bone, and other biocompatible and/or bone regenerative materials naturally occurring or man-made materials. Each of the structures can also be supplemented with biocompatible and/or bone/tissue regenerative materials, such as meshes or platings that can be attached or formed on surfaces of the structures or inserted into the central axis CA and other openings in the structures. The structures 10, 20, 30 can be made from the same or different material depending on particular applications and desires of a user. In addition, the pins and set screws can be made of the same or different materials relative to each other and other components of the implant 1.

Although the pins are shown as cylindrical bar shaped structures, there are many different shapes, sizes and styles of structures that can be used to cause the desired relative motion between the components of the implant 1. For example, the pins can be polygonal in cross section, non-symmetrical, etc. In addition, the pins could be bent or include different shapes that are helpful in particular applications. The pins could be formed integrally with other parts of the implant or can be separate structures. In addition, the pins can be attached in many various ways to other components of the implant 1, for example, via adhesives, welding, bearings, etc.

With respect to the various methods that can be used to practice the presently disclosed subject matter, it is contemplated that the specific steps can be executed sequentially, but can also be executed simultaneously and/or in reverse or other orders. Relative rotation between the structures 10, 20, and 30 can be in either rotational direction without departing from the scope of the disclosed subject matter.

The implant 1 as depicted can be used for the lumbar, thoracic or even cervical region of the spinal column. However, it is contemplated that the disclosed subject matter could be employed in other areas of the spinal column or skeletal system. The device, system and method can be used in vivo on human beings but can also be used for teaching purposes in cadavers, and plastic or other model spinal columns. In addition, the device, system and method can be used in veterinarian practices for invertebrate animals.

The specific components of each of the exemplary embodiments depicted can be used in conjunction with other embodiments or in replacement of other similar structures from the other various embodiments. For example, the gear teeth 25 and window 17W can be provided on any of the disclosed and described embodiments. In addition, any of the embodiments can include grooves 32 or 32C that either extend all the way through the bottom structure wall or extend partially into the bottom structure wall from an exterior surface. Thus, any of the pins can be single or multiple pin structures. In addition, while two pins are shown for certain of the structures, three or more pins could be used if highly accurate or slower movement is desired between the structures. Furthermore, while the pins are shown as being press-fit into accessways, the pins could be attached using various other structures or attachment strategies. For example, bearings could be provided at each or some of the accessways to securely fit the pin(s) to the accessway while permitting rotation of the pin. Adhesives, welding, bonding, and other attachment methods can be utilized to attach the pin(s). In addition, in lieu of a set screw arrangement, various other structures could be used to lock the top, bottom and intermediary structures relative to each other. For example, a weld or an adhesive could be used to lock the structures 10, 20, 30 together once in position. Alternatively, a clamp, clasp, cam, or button lock could be used, as well as other known attachment or locking structures, to provide the locking feature.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. An implant device configured to be inserted between adjacent skeletal components, comprising:
    a top structure including a top facing surface;
    a bottom structure including a bottom facing surface substantially opposed to the top facing surface; and
    an intermediary structure configured to be rotatable with respect to at least one of the bottom structure and the top structure, and about a central axis extending from the top facing structure to the bottom facing structure, wherein the bottom structure includes a first guide structure and a second guide structure,
        the first guide structure is configured to guide the intermediary structure in both a rotational direction about the central axis and an axial linear direction along the central axis when the intermediary structure is rotated, and
        the second guide structure is configured to guide the top structure in the axial linear direction along the central axis when the intermediary structure is rotated,
    wherein the first guide structure is a helical groove defined in the bottom structure.

2. The implant device of claim 1, wherein the bottom structure is a tubular structure with an outer surface and an inner surface defining a central opening extending along the central axis, and the helical groove extends entirely through the tubular structure from the outer surface to the inner surface to form a dynamic spring structure located between the bottom facing surface of the bottom structure and an opposing end surface of the bottom structure.

3. The implant device of claim 1, wherein the bottom structure is a tubular structure with an outer surface and an inner surface defining a central opening extending along the central axis, and the helical groove extends partially through the tubular structure from the outer surface towards the inner surface.

4. The implant device of claim 1, wherein the second guide structure is a linear groove defined in the bottom structure.

5. The implant device of claim 1, wherein the top structure is a tubular structure having an opening extending along the central axis, and the top structure includes at least one pin structure located in the opening and extending substantially perpendicular with respect to the central axis.

6. The implant device of claim 5, wherein the at least one pin extends entirely across the opening in the tubular structure.

7. The implant device of claim 5, wherein the at least one pin extends from an interior wall of the opening in the tubular structure and terminates at a location that is less than half of a width of the opening in the tubular structure of the top structure.

8. The implant device of claim 1, wherein the top structure includes a set screw configured to lock the top structure with respect to the bottom structure such that that top structure is fixed and cannot move relative to the bottom structure when the set screw is actuated.

9. The implant device of claim 1, wherein the top structure includes a window defined therein, and the intermediary structure includes a motion structure that is accessible via the window of the top structure, the motion structure configured to move the top structure relative to the bottom structure when actuated.

10. An implant device configured to be inserted between adjacent skeletal components, comprising:
    a top structure including a top facing surface;
    a bottom structure including,
        a bottom facing surface substantially opposed to the top facing surface and located at a first end of the bottom structure,
        an opposing surface opposed to the bottom facing surface and located at a second end of the bottom structure opposed to the first end, and
        a helical groove structure defined between the bottom facing surface and the opposing surface of the bottom structure and about a central axis; and
    an intermediary structure including at least one pin extending from the intermediary structure and into the helical groove structure such that, when the intermediary structure is rotated with respect to at least one of the bottom structure and the top structure, the pin and the helical groove structure guide the intermediary structure to move in both a rotational direction about the central axis and in an axial linear direction along the central axis.

11. The implant device of claim 10, wherein the bottom structure includes a linear groove extending substantially parallel with the central axis.

12. The implant device of claim 11, wherein the bottom structure is a tubular structure with an outer surface and an inner surface defining a central opening extending along the central axis, and the helical groove extends entirely through the tubular structure from the outer surface to the inner surface to form a dynamic spring structure located between the bottom facing surface of the bottom structure and an opposing end surface of the bottom structure.

13. The implant device of claim 10, wherein the bottom structure is a tubular structure with an outer surface and an inner surface defining a central opening extending along the central axis, and the helical groove extends partially through the tubular structure from the outer surface towards the inner surface.

14. The implant device of claim 10, wherein the intermediary structure includes an annular groove defined in an exterior surface of the intermediary structure, and the top structure includes at least one pin extending into the annular groove in the intermediary structure.

15. The implant device of claim 10, wherein the top structure is a tubular structure having an opening extending along the central axis, and the top structure includes at least one pin structure located in the opening and extending substantially perpendicular with respect to the central axis.

16. The implant device of claim 15, wherein the at least one pin extends entirely across the opening in the tubular structure.

17. The implant device of claim 15, wherein the at least one pin extends from an interior wall of the opening in the tubular structure and terminates at a location that is less than half of a width of the opening in the tubular structure of the top structure.

18. The implant device of claim 10, wherein the top structure includes a set screw configured to lock the top structure with respect to the bottom structure such that that top structure is fixed and cannot move relative to the bottom structure when the set screw is actuated.

19. The implant device of claim 10, wherein the top structure includes a window defined therein, and the intermediary structure includes a motion structure that is accessible via the window of the top structure, the motion structure configured to move the top structure relative to the bottom structure when actuated.

20. The implant device of claim 10, wherein the motion structure includes a set of gear teeth located about a periphery of the intermediary structure.

\* \* \* \* \*